United States Patent [19]
Cox

[11] Patent Number: 5,467,760
[45] Date of Patent: Nov. 21, 1995

[54] PORTABLE SPORTSMAN FURNACE

[76] Inventor: John H. Cox, 2005 Alanson St., Westland, Mich. 48185

[21] Appl. No.: 340,607

[22] Filed: Nov. 16, 1994

[51] Int. Cl.$^6$ ..................................................... A61F 7/08
[52] U.S. Cl. ........................... 126/208; 126/204; 126/248
[58] Field of Search .................................... 126/204, 206, 126/208, 209, 248, 4, 93, 59, 43

[56] References Cited

U.S. PATENT DOCUMENTS

| | | | |
|---|---|---|---|
| 2,698,646 | 1/1955 | Hepworth | 126/204 |
| 3,024,782 | 3/1962 | Knopps | 126/208 |
| 3,509,866 | 5/1970 | Singleton | 126/208 |
| 4,691,688 | 9/1987 | Urso | 126/208 |
| 4,860,726 | 8/1989 | Barker | 126/208 |
| 5,121,739 | 6/1992 | Barker | 126/248 |

FOREIGN PATENT DOCUMENTS

| | | | |
|---|---|---|---|
| 44021 | 3/1910 | Germany | 126/208 |

*Primary Examiner*—James C. Yeung

[57] ABSTRACT

A portable sportsman furnace wherein a unitary housing is arranged for selective securement to an external propane fuel supply, wherein an internal valving permits preselected fuel flow and heating of the burner assembly within the housing to a predetermined level of fuel consumption, and wherein a baffle assembly within the housing permits even distribution of heating throughout the housing, such that louvered vent openings permit ease and consistent distribution of heat throughout a surrounding area relative to the furnace of the invention.

5 Claims, 4 Drawing Sheets

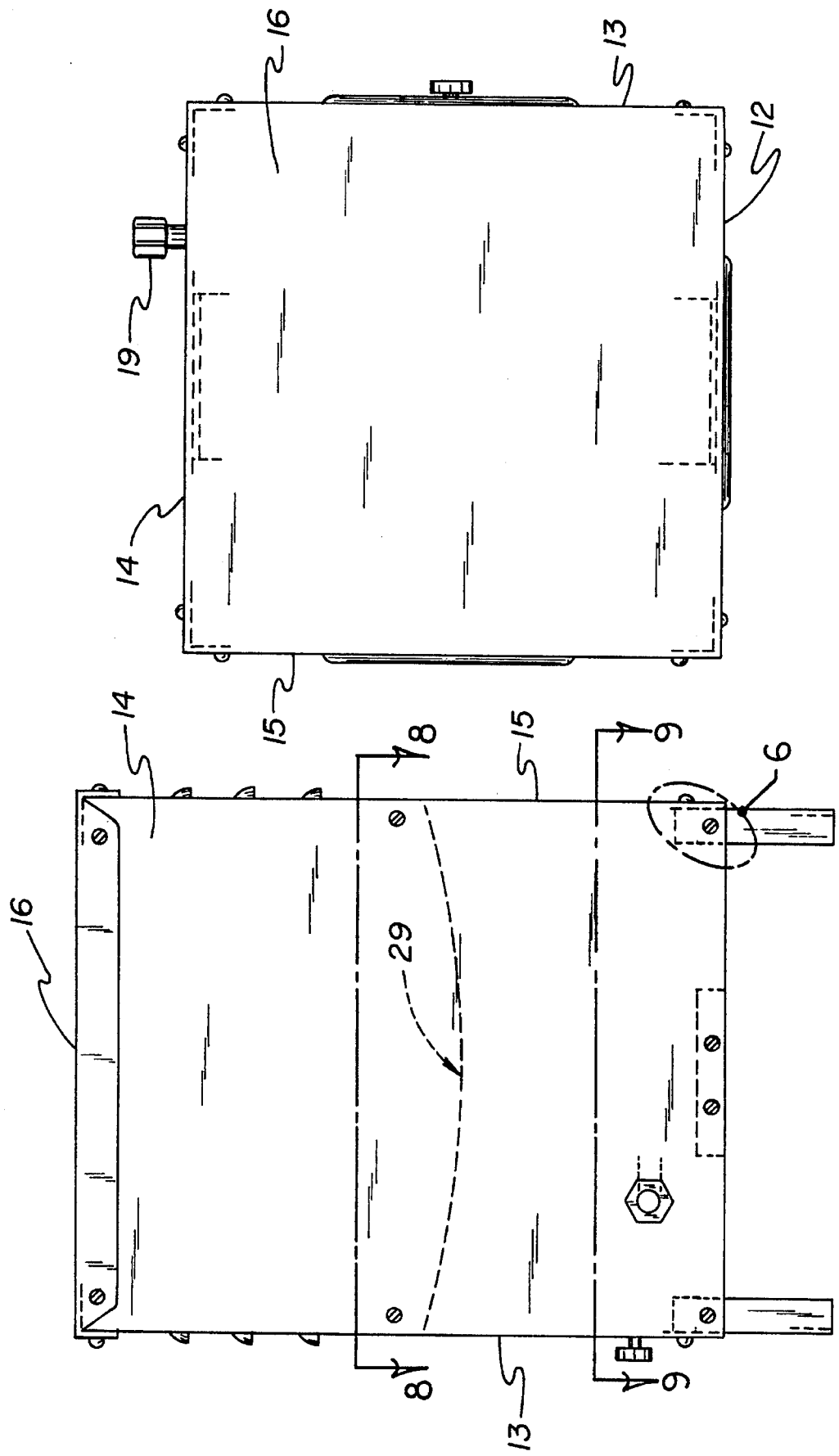

FIG. 5
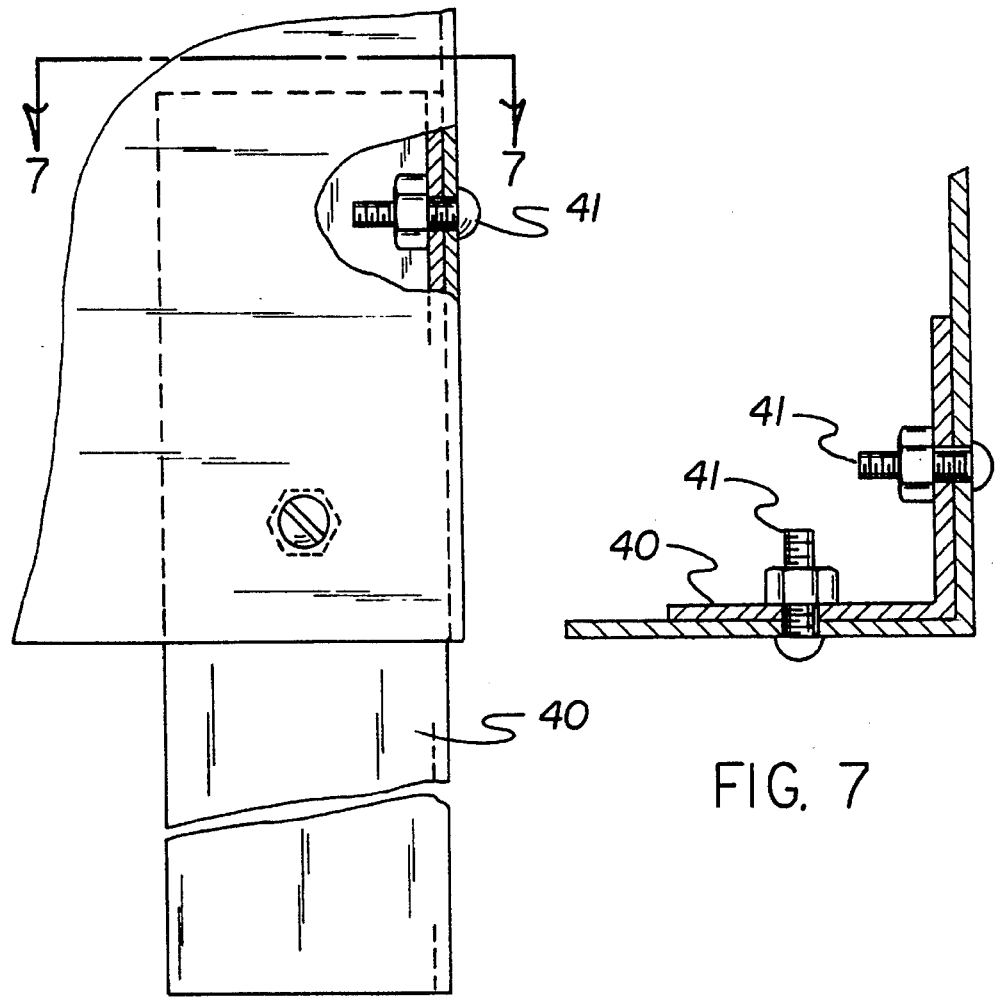
FIG. 6
FIG. 7

PORTABLE SPORTSMAN FURNACE

TECHNICAL FIELD

The field of invention relates to furnace apparatus, and more particularly pertains to a portable sportsman furnace permitting ease of portability in utilization of the furnace structure of the invention in various sporting events such as hunting, fishing, and the like.

BACKGROUND OF THE INVENTION

Prior art furnace structure such as portable furnace structure for use with bottled liquid propane is indicated by the U.S. Pat. No. 3,590,806, with a gas heater in U.S. Pat. No. 3,846,616 indicated for use as a portable gas heater arrangement, with U.S. Pat. No. 3,689,040 indicating a portable space heater and gas burner utilizing a high-velocity air stream from within the gas burner structure. U.S. Pat. No. 4,512,328 sets forth a portable gas heating unit useful for heating food and the like.

SUMMARY OF THE INVENTION

The present invention relates to a portable sportsman Furnace wherein the same is employed by various sportsmen for utilization in various sporting events such as deer hunting blinds, ice fishing shanties, and other outdoor enclosures, with a single housing arranged for selective securement to a liquid petroleum bottle typically employing a regulator to direct such LP gas to the invention, wherein the housing of the invention employs louvered side walls and unique baffle arrangement to effect even dispersion of heated air within the furnace structure.

Objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and Features thereof.

BRIEF DESCRIPTION OF THE DRAWINGS

FIG. 3 is an orthographic rear view of the invention.

FIG. 4 is an orthographic top view of the invention.

FIG. 5 is an orthographic view, taken along the lines 5—5 of FIG. 2 in the direction indicated by the arrows, indicating a louver construction.

FIG. 6 is an enlarged, orthographic view of section 6 as set forth in FIG. 3.

FIG. 7 is an orthographic view, taken along the lines 7—7 of FIG. 6 in the direction indicated by the arrows.

DESCRIPTION OF THE PREFERRED EMBODIMENT

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 2:
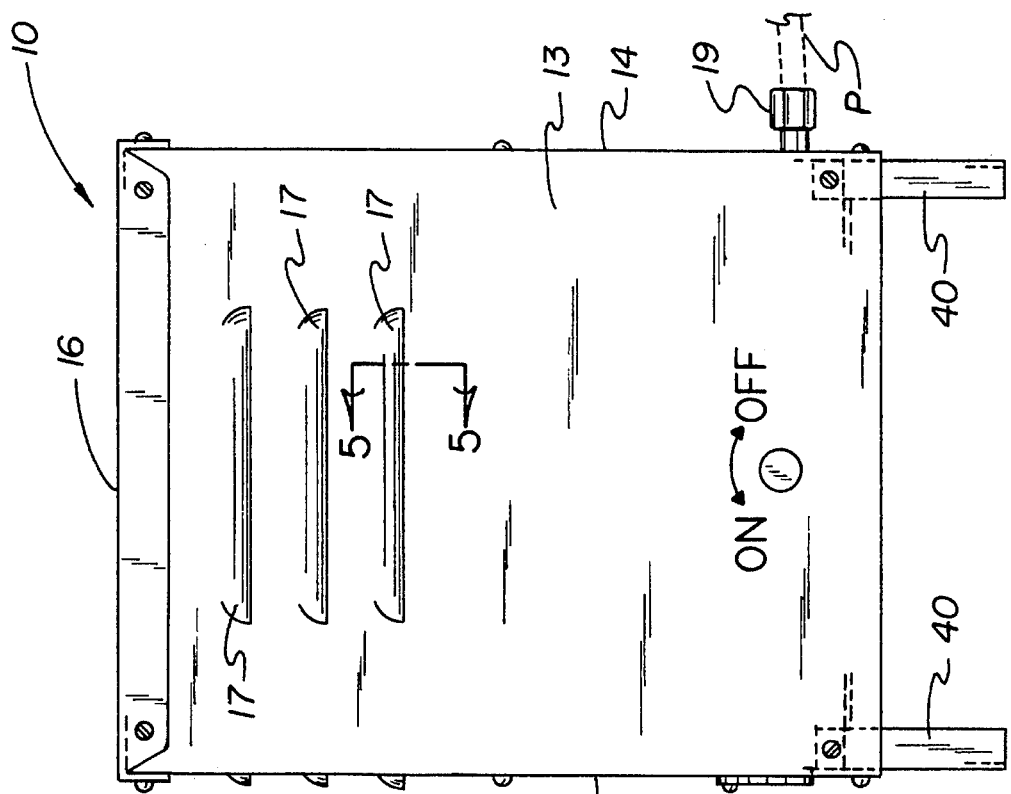
FIG. 2 is an orthographic right side view of the invention.
Figure 1:
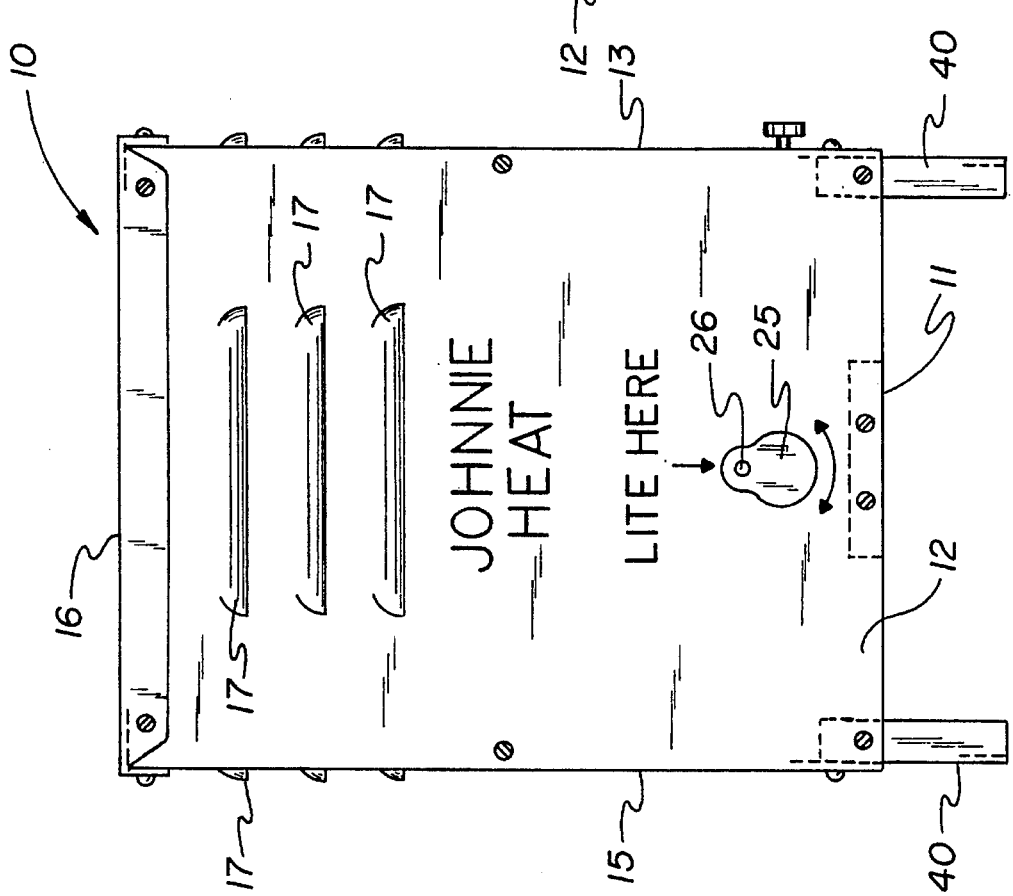
FIG. 1 is an orthographic front view of the invention.
Figure 8:
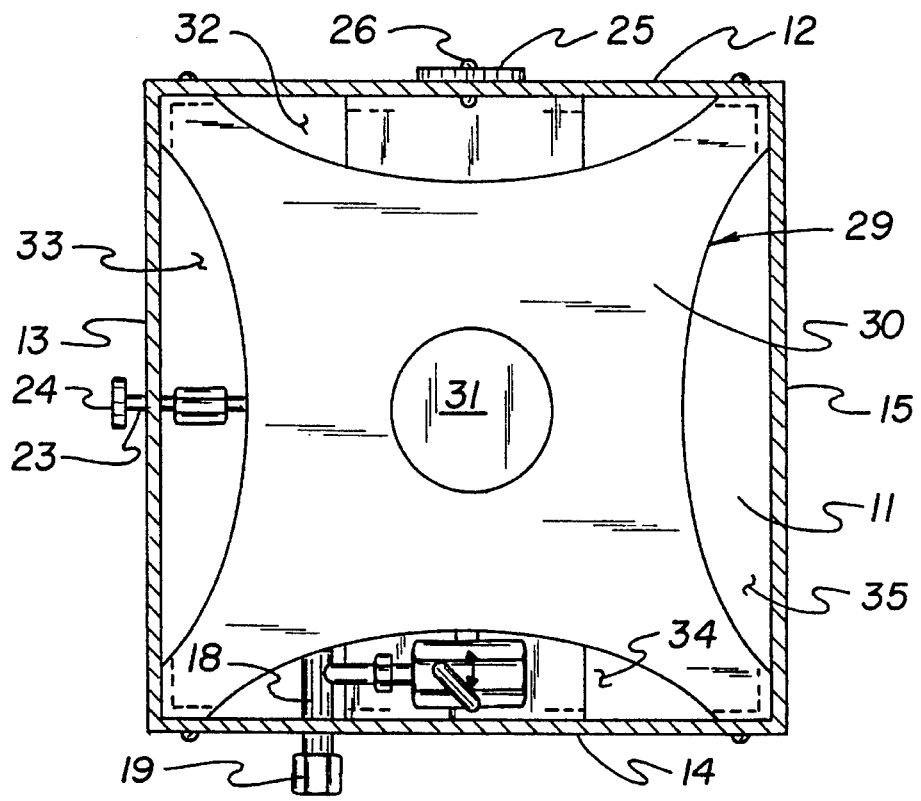
FIG. 8 is an orthographic view, taken along the lines 8—8 of FIG. 3 in the direction indicated by the arrows.
Figure 9:
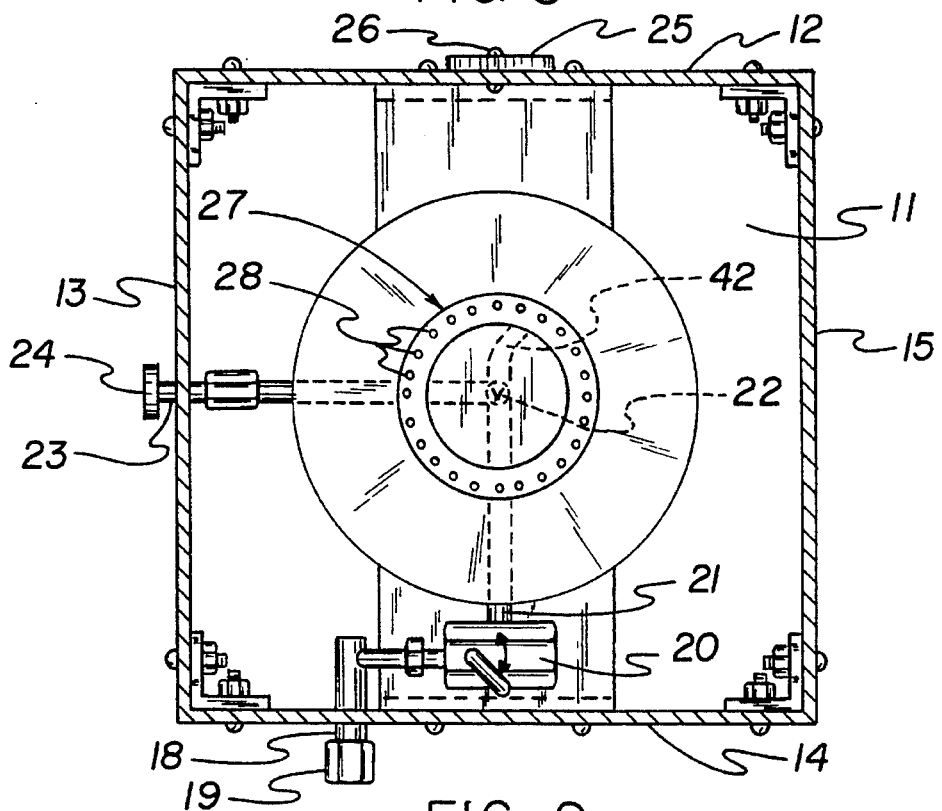
FIG. 9 is an orthographic view, taken along the lines 9—9 of FIG. 3 in the direction indicated by the arrows.

The portable furnace 10 of the invention includes a unitary housing having a floor 11 spaced from a top wall 16, with a surrounding side wall including respective first, second, third, and fourth walls 12, 13, 14, and 15 respectively. A plurality of the walls include a row of louvered vent openings constructed of a type as indicated in FIG. 5, wherein each of the vent openings includes an overhang to prevent rainwater and the like from being directed into the housing, as well as directing the heat initially downwardly from within the overhang to assist in the circulation of heat relative to the unitary housing structure. Fuel for the furnace is typically of a thirty or forty pound bottle having a regulator directing such gas to a coupler 19 of a first conduit 18 from a propane fuel line "P", such as illustrated in FIG. 2. The first conduit 18 directs the propane to a second conduit 21 through a second valve 22 that permits the control of gas flow into the burner assembly 27 of the invention. It is understood that a power light may be employed but for purposes of safety, such is not included herewith, wherein a control rod 23 having a handle 24 directed exteriorly of the second wall 13 permits mechanical on/off action of the second valve 22 that controls gas flow to the burner ports 28 of the burner assembly 27 through a third conduit 42. A door plate 25 pivotal about a door plate axle 26 is displaced to permit access through an associated opening through the first wall 12 providing for ease of lighting of the burner assembly 27 by an external source such as a match and the like.

A baffle plate 29 having a concave wall 30 in facing relationship relative to the top wall 16 is oriented between the burner assembly 27 and the top wall, and more specifically between the burner assembly and the rows of louvered vent openings 17. The baffle plate 29 includes a central opening 31 coaxially aligned relative to the burner assembly 27, as well as providing for first, second, third, and fourth gaps 32, 33, 34, and 35 respectively oriented between the baffle plate 29 and the respective first, second, third, and fourth walls 12–15. The aforenoted first through fourth gaps 32'35 are defined by respective first, second, third, and fourth arcuate side walls 36, 37, 38, and 39 respectively of the baffle plate, with the first arcuate side wall 36 arranged for example in facing relationship relative to the first wall 12 to define the first gap 32. In this manner, the unique configuration of the baffle plate assists in heat distribution throughout the housing of the furnace structure 10.

Leg members are oriented at each of the corners utilizing fasteners 41 or otherwise welding, adhesives and the like may be employed relative to the fastening of the legs to the housing to permit the spacing of the floor 11 relative to an underlying surface to further assist in heat distribution and maximize heat distribution from the portable sportsman furnace 10 of the invention.

It is to be understood that while certain forms of the present invention have been illustrated and described herein, it is not to be limited to the specific forms or arrangement of parts described and shown.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed and desired to be protected by LETTERS PATENT of the United States is as follows:

1. A portable sportsman furnace, comprising, a unitary housing having a floor spaced from a top wall, with a continuous side wall member, including a first wall spaced from a third wall, with a second wall spaced from a fourth wall, with the second wall and the fourth wall oriented between the first wall and the third wall, and at least the first wall having a vent opening, and burner means positioned within the housing adjacent to the floor, with the burner means oriented between the vent openings and the floor for directing heat throughout the housing and directing the heat through the vent opening, the burner means includes a burner assembly, with the burner assembly having an array of burner ports, and a first conduit extending through the third wall, and the first conduit having a coupler oriented exteriorly of the third wall for securement to a fuel line selectively, with the first conduit having a first valve, and a second conduit extending from the first valve to a second valve, and a control rod extending through the second wall to the second valve to control fuel flow therethrough, and a third conduit extending from the second valve to the burner ports.

2. A furnace as set forth in claim 1 including an opening directed through the first wall, with a door having a door axle, and the door positioned overlying the opening in a first position and displaced relative to the opening in a second position to permit access to the burner assembly for permitting ignition of the burner assembly.

3. A furnace as set forth in claim 2 with a baffle plate positioned within the housing fixedly, and the baffle plate oriented between the burner assembly and the vent openings.

4. A furnace as set forth in claim 3 wherein the baffle plate includes a concave wall in facing relationship relative to the top wall, and the baffle plate having a central opening oriented medially over the burner assembly.

5. A furnace as set forth in claim 4 wherein the baffle plate includes a first arcuate side wall defining a first gap between the first arcuate side wall and the first wall, and the baffle plate having a second arcuate side wall defining a second gap between the second arcuate side wall and the second wall, and the baffle plate further having a third arcuate side wall defining a third gap between the third arcuate side wall and the third wall, and the baffle plate further having a fourth arcuate wall defining a fourth gap between the fourth arcuate side wall and the fourth wall.

* * * * *